United States Patent
Neuberger

(10) Patent No.: US 6,948,815 B2
(45) Date of Patent: Sep. 27, 2005

(54) LASER SAFETY CONTACT LENSES

(75) Inventor: Wolfgang Neuberger, F.T. Labuan (ML)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 10/628,522

(22) Filed: Jul. 28, 2003

(65) Prior Publication Data

US 2005/0024583 A1 Feb. 3, 2005

(51) Int. Cl.⁷ ................................................ G02C 7/04
(52) U.S. Cl. ............................. 351/162; 351/160 R
(58) Field of Search ........................ 351/160 R, 160 H, 351/161, 162; 606/4–6

(56) References Cited

U.S. PATENT DOCUMENTS

| | | | |
|---|---|---|---|
| 4,194,814 A | | 3/1980 | Fischer et al. ......... 351/160 R |
| 4,616,910 A | | 10/1986 | Klein ......................... 351/162 |
| 4,744,647 A | | 5/1988 | Meshel et al. .............. 351/177 |
| 4,848,894 A | | 7/1989 | Buser et al. ................ 351/162 |
| 4,971,433 A | * | 11/1990 | Neefe ......................... 351/162 |
| 5,059,018 A | * | 10/1991 | Kanome et al. ............ 351/162 |
| 5,120,121 A | * | 6/1992 | Rawlings et al. ........... 351/162 |
| 5,617,154 A | * | 4/1997 | Hoffman .................... 351/162 |
| 6,059,775 A | * | 5/2000 | Nielsen ......................... 606/5 |
| 6,164,777 A | | 12/2000 | Li et al. .................... 351/162 |
| 6,488,375 B2 | | 12/2002 | Streibig ..................... 351/162 |
| 6,494,575 B1 | * | 12/2002 | Jahnke ....................... 351/162 |
| 2002/0003605 A1 | | 1/2002 | Rogers et al. ......... 351/160 R |

* cited by examiner

Primary Examiner—Jordan M. Schwartz
(74) Attorney, Agent, or Firm—B J Associates; Bolesh J. Skutnik

(57) ABSTRACT

Individually marked contact lenses for protection of one's eyes from harmful radiation are provided. Contact lenses are coated or treated to be absorptive or reflective to a preselected wavelength or wavelengths. The lenses contain one or more identification areas on each lens to demonstrate that the lenses are being worn and to indicate the proper applications with which the lenses should be used and/or the wavelengths for which the lens is protective. The identification area, which should be visible when worn to third parties and/or the person wearing the lenses, consists of markings such as colored bands or shaded areas in the region around the iris. Different colors or color patterns of the markings indicate which wavelengths the lens protects against. Other safety features may include fluorescent markers, added features and devices to facilitate placement and retention in the eye, pick-up or release.

12 Claims, 1 Drawing Sheet

LASER SAFETY CONTACT LENSES

BACKGROUND OF THE INVENTION

1. Field of the Invention

The present invention relates to safety eyewear for use during laser applications, particularly contact lenses for laser safety.

2. Information Disclosure Statement

An important consideration in radiation or laser applications is the safety of the practitioner or user, as well as the safety of those proximate to the radiation source. In medical settings, both a practitioner and support staff must use sufficient precautions to ensure that they do not sustain injuries due to accidental radiation exposure. Of particular concern is the safety of the eyes of those near the laser or radiation source. Errantly directed radiation can cause significant and lasting damage to a person's eye. This damage can take many forms. If a beam used for cutting or vaporizing tissue is directed toward the eye, it could cause damage by cutting the eye. Certain wavelengths are particularly well-absorbed by ocular tissue or blood vessels, and can cause direct or thermal destruction. The damage may be considerable, long-lasting, and could damage vision.

Current state of the art laser eye protection is characterized by mostly bulky laser safety eye glasses that must be worn during laser or radiation applications. For instance, during medical laser treatment procedures, both the doctor(s) carrying out the procedure, support staff, and in many cases the patient must wear these eye protection devices. This constitutes an inconvenience for the doctor and staff in that it may impede vision, for instance when looking through microscopes or when additional vision correction is involved. In the latter case bulky safety glass designs may be required to fit over the vision correction glass.

Alternatives to safety glasses include contact lenses treated to reflect or absorb harmful radiation. This offers the advantage of removing the inconvenience of glasses. If some safety glasses are still desired, for instance to protect the eyes from dust, smoke, or other material, those who require vision correction no longer have to wear large safety glasses over their eyes. Small, light glasses may be used instead.

U.S. Pat. No. 4,848,894 describes a contact lens with laser protection properties. These properties are accomplished by embedding a reflecting or absorbing layer in the lens material, or applying such layer to the convex surface of the lens. The layer may be a Fabry-Perot reflector or a thin film or holographically formed reflective or absorptive interference filter, or an absorbing layer. The disclosure does not include ways to identify the lens as to what wavelengths it protects from, nor does it have any indicators to alert others that the lenses are being worn.

A major disadvantage of contact lenses are that they are very difficult to see, especially after being placed in the eye. It would be difficult for a person to visually confirm whether those near a radiation source are using the safety lenses, unlike conventional safety glasses that are prominent and easy to see when worn. Also, because of their small size and transparency, it may be difficult to distinguish one contact lens for another. This is especially important where lenses are custom made to protect the eye from certain types of radiation, and thus it is important that the correct lens be worn for a specific procedure.

A number of devices and methods have been disclosed for marking contact lenses. Such markings are generally for identifying specific lenses or identifying the front or back surface of the lens, identifying the right or left eye, identifying the proper orientation for toric lenses, and providing prescription information.

U.S. Patent Application No. 2002/0003605 discloses contact lenses with visible marking indicia. The indicia are formed by etching a number of small recessed spots on a surface of the lens to create a visible marking. These markings appear to be primarily intended to allow one to identify specific lenses prior to placement on the eye. There is no indication that such marks would be visible when worn. The markings disclosed would not be easily seen while the lens is located on the eye. The markings are small, colorless, and generally positioned on the periphery of the lens. It would likely be very difficult to see these markings when the lenses are worn, because it is very difficult for the wearer to control rotation of the lens on the eye, and thus the markings may likely be obscured by the eyelids. Additionally, the recesses may also fill with fluid when worn, further decreasing visibility. These factors, in addition to the small size of the markings, make it virtually impossible to ensure that the markings can be visible without close inspection when the lenses are worn.

U.S. Pat. No. 4,616,910 describes a contact lens with a visual indicator to show that the lens is not inside-out. The indicator has the characteristic that it looks different when viewed from the outside surface versus the inside surface of the lens. This marking is intended to be visible to a user prior to being worn. Because of its small size and potential to be hidden behind the eyelids, the indicator would not be visible after the contact is worn.

U.S. Pat. No. 4,194,814 discloses methods for sublimating lens material to create identifying symbols or indicia. A high intensity laser beam is used for creating the indicia by engraving markings on the surface of the lens. These methods produce markings that would not be visible during use, due to either size and location or due to the fact that the engraved areas fill with fluid.

Markings that are made by etching are restricted in that they have to be sufficiently small and at a location on the lens (the periphery) so that the vision of the user is not affected. Also, when the indentations fill with fluid after being put on the eye, this could serve to reduce reflection off the indentations and reduce visibility further. This severely limits the potential of these methods for providing indicia that is easily identifiable while the lens is worn.

U.S. Pat. No. 4,744,647 provides a method for forming a semi-opaque region on a contact lens. The semi-opaque region can be colored, or can form a coded symbol. The method can be used for cosmetic reasons, by forming a semi-opaque region over the iris region, and coloring it to change the apparent color of the iris. It can also be used to form various symbols on the eye, such as to signal left and right eye. Such symbols would probably be small and be on the periphery of the lens. This method would not be desirable for laser safety systems, in that the entire eye must be protected, and forming semi-opaque regions could compromise the ability of the lens surface to protect the eye from harmful radiation.

Patents exist for tinted contact lenses and methods for tinting such lenses, such as U.S. Pat. Nos. 6,164,777 and 6,488,375. These inventions are generally for cosmetic alterations of eye color and are not contemplated as laser safety lenses.

The prior art has not disclosed a contact lens for protection from harmful radiation that additionally features identifying indicia that are highly visible when placed in the eye. Therefore, there exists a need for contact lens specially manufactured to protect a practitioner from radiation during laser or radiation applications, that additionally contains highly visible and easily recognizable indicia to indicate clearly and from a distance that the practitioner is wearing the lenses and that they are the proper protection for a given application.

OBJECTIVES AND BRIEF SUMMARY OF THE INVENTION

It is an object of the present invention to provide laser protective contact lenses that are easily visible to third parties and/or the user while worn.

It is another object of the present invention to provide laser protective contact lenses that can easily be verified as proper or improper for a given radiation wavelength.

Briefly stated, the present invention provides individually marked contact lenses for protection of a person's eyes from harmful radiation. Contact lenses are coated or treated to be absorptive or reflective to a preselected wavelength or wavelength range. The lenses are for protection and generally do not provide vision correction. Because different lenses may protect against different wavelengths and are thus suitable only for certain applications, and because it is desirable to be able to visually confirm that all those in vicinity of the radiation are wearing the proper lenses, the lenses contain one or more identification areas on each lens to demonstrate that the lenses are being worn and to indicate the proper applications with which the lenses should be used. The identification area, which should be visible when worn, to third parties and/or the person wearing the lenses, consists of markings such as colored bands or shaded areas in the region around the iris. Different colors or patterns indicate which wavelengths the lens protects against. Other safety features are contemplated, such as fluorescent markers, added features and devices to facilitate placement in the eye, pick-up or release and to prevent the lens from accidentally dropping out.

The above, and other objects, features and advantages of the present invention will become apparent from the following description read in conjunction with the accompanying drawings, (in which like reference numbers in different drawings designate the same elements.)

DETAILED DESCRIPTION OF PREFERRED EMBODIMENTS

Figure 1A:
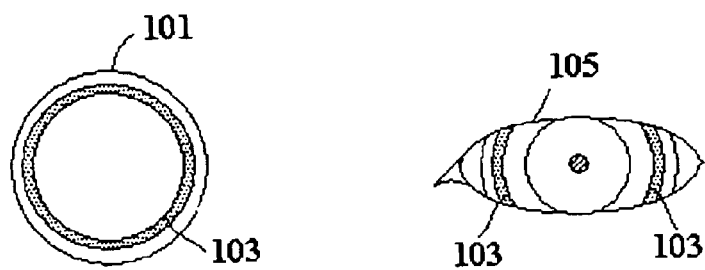
FIG. 1—Illustration of preferred safety contact lenses and their appearance when worn on the eye.

The present invention provides improved safety contact lenses that may be worn conveniently by practitioners and those proximate to a radiation source during a medical treatment or other procedure. The lenses of the present invention increase safety by allowing others, or the person wearing the lenses, to quickly visually confirm that the proper safety contact lens are being worn for a given procedure.

Contact lenses are disclosed in the present invention that provide a convenient way to protect the eyes of practitioners, support staff and patients from ocular exposure to harmful radiation during laser applications or medical treatments. They allow the user to perform laser procedures without the distraction of often bulky safety glasses, allow easy use of visual instruments such as microscopes, and avoid problems such as scratches or accumulation of material on safety glasses that could compromise visibility.

It is a further part of the present invention to have unique identification areas, or markings on the safety lenses to indicate the characteristics of the lens. Different lenses are designed for different levels of protection and for protection from different wavelengths. Such markings can be customized to each type of protective lens, and indicate what the protection level of the lens is and what wavelengths it can protect against, so that a user can be assured that the proper lens is being used. It is preferable that the marking be visible while the lens is worn, so that others may visually confirm that all those in proximity to a harmful radiation source are wearing the protective contact lenses.

The contact lenses of the present invention are coated with suitable filters (usually interference filters) and/or incorporate suitable absorbers into the material they are composed of to attenuate any incoming potentially harmful (laser) radiation down to an eye safe level meeting safety and legal requirements. The lenses are generally, but not necessarily, made vision-correction neutral, so as to appeal to a broad part of the relevant persons. They can be single-day wear or reusable. Special lenses including a degree of vision correction can be manufactured as well. For example, a practitioner such as a dentist can have numerous sets of corrective contact lenses, each specifically marked for each type of laser procedure that may be performed.

The safety contact lenses also contain an identification area consisting of one or more distinctive markings to give a clear indication as to which laser type and radiation they are protecting against, to avoid mistakes and possibly injury. In a preferred embodiment, a colored, clearly visible ring on the circumference of the lens would help to show to other personnel present that the respective protection lenses are worn. A colored marking can be accomplished by, for example, coating a preselected portion of the lens with a specific color material, impregnating specific portions of the contact lens material with a dye, or by known printing methods. Other markings are also contemplated, such as specific shaded or opaque areas. Shading can be accomplished by altering the surface texture of the lens in specific areas so that those areas appear darker than the remainder of the transparent lens. In one example, creating an array of small recessed spots can increase opacity in a given area. Other possible safety features can be added, such as fluorescent markers, added features and devices to facilitate placement and pick-up or release and prevent accidental drop-out.

Other indicative markings include a reflective coating, or a dye that is only visible under certain light, such as UV. In that embodiment, a low intensity UV light source could be used to view the markings and determine whether the proper contact lens has been chosen. This would allow larger and more numerous markings than would be possible with visible markings, in that the markings would not interfere with vision while the contacts are worn.

In another preferred embodiment, the markings are of a variety of colors or patterns to indicate the protective capabilities of the contact lens. Each color and/or pattern is preselected to correspond to a different level of protection or a different wavelength or wavelength range for which the lens is protective. A predetermined scheme of colors and/or patterns is provided so that users know in advance which treatment or set of laser parameters correspond to a given set of protective contact lenses. In this way, in addition to confirming that a protective lens is actually being worn, a practitioner can also visually verify that each person involved in a given treatment is wearing the proper safety contact lens for that treatment.

Figure 1B:
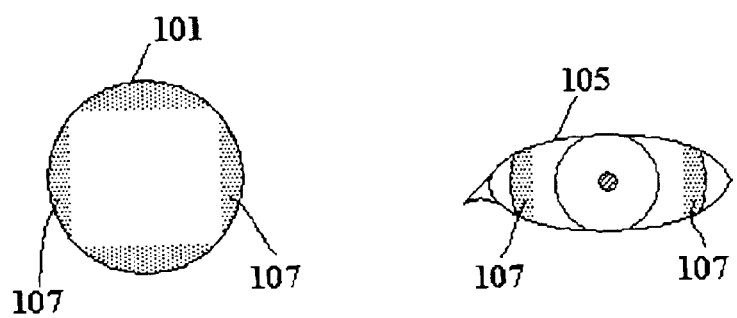
Figure 1C:
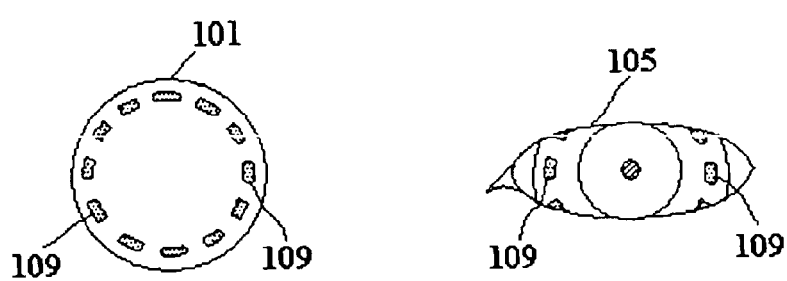

Examples of preferred embodiments are illustrated in FIGS. 1a–c. Referring to FIG. 1a, contact lens 101 is coated with a material to reflect or absorb a preselected wavelength or wavelength range. Alternatively, the material from which contact lens 101 is constructed is itself reflective or absorptive of the preselected wavelength or range of wavelengths. Tinted ring 103 is located near the periphery of contact lens 101, at a location that would not interfere with vision when worn in eye 105. After insertion of contact lens 101 into eye 105, ring 103 is clearly visible. Thus, it can be quickly verified by others, or by the user, that the user is indeed wearing contact lens 101. Additionally, ring 103 is of a color corresponding to a given wavelength or wavelength range, and thus it can be easily verified that the proper protective lens is worn for a given treatment. In another embodiment, shown in FIG. 1b, a differently shaped marking 107 can be used to differentiate the lens. Another example of an alternate marking pattern 109 is shown in FIG. 1c. By providing a variety of available marking patterns and colors, individualized protective lenses marked for a variety of radiation types and procedure can be produced.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A safety contact lens comprising:
   means to protect an eye from harmful radiation;
   at least one identification area on said lens;
   wherein said identification area is visible to third parties, to a person wearing said lens, or both while said lens is worn on an eye;
   wherein said identification area is a tinted area of a color; and
   wherein said color is chosen to corresponding to at least one radiation parameter to which said contact lens is protective according to a preselected scheme.

2. A safety contact lens comprising:
   means to protect an eye from harmful radiation;
   at least one identification area on said lens;
   wherein said identification area is visible to third parties, to a person wearing said lens, or both while said lens is worn on an eye; and
   wherein said identification area is a tinted area that is not visible under light in the normal visible range, and is only visible under light of a preselected wavelength range.

3. The safety contact lens according to claim 2, wherein said light of a preselected wavelength range is ultraviolet light.

4. A safety contact lens comprising:
   means to protect an eye from harmful radiation;
   at least one identification area on said lens;
   wherein said identification area is visible to third parties, to a person wearing said lens, or to both while said lens is worn on an eye; and
   wherein said identification area has visual attributes that vary according to given radiation parameters, and wherein said visual attributes are unique to a given treatment or set of radiation parameters according to a preselected scheme.

5. A safety contact lens comprising:
   means to protect an eye from harmful radiation, wherein said harmful radiation is from a man-made source;
   at least one identification area on said lens for the purpose of providing safety information;
   wherein said identification area is clearly visible to third parties or to a person wearing said lens or both while said lens is worn on an eye; and
   wherein said identification area is located outside an area of the iris of said eye when said contact lens is worn on said eye.

6. The safety contact lens according to claim 5, wherein said identification area is selected from the group consisting of a shaded area and a tinted area.

7. The safety contact lens according to claim 6, having said shaded area, wherein said shaded area is an area having altered surface texture so as to increase opacity of said shaded area.

8. The safety contact lens according to claim 5, wherein said identification area is located at a position on said contact lens that does not overlay a pupil of said eye.

9. The safety contact lens according to claim 5, wherein said identification area is in the form of a ring at or near a periphery of said contact lens.

10. A safety contact lens according to claim 5 wherein said harmful radiation from said man-made source is laser radiation.

11. A safety contact lens according to claim 10 wherein said harmful radiation from said man-made source is high power laser radiation.

12. A safety contact lens according to claim 5 wherein said means to protect an eye includes coating(s) of suitable filters and/or suitable absorbers onto said lens to attenuate incoming harmful radiation from said man-made source to an eye safe level meeting safety and legal requirements.

* * * * *